United States Patent [19]

Ter-Minassian et al.

[11] 4,055,982
[45] Nov. 1, 1977

[54] CALORIMETERS FOR MAKING MEASUREMENTS AT PRESSURES ABOVE 1000 BARS

[75] Inventors: Léon Ter-Minassian, Fresnes; Philippe Pruzan, L'Hay-les-Roses; Pierre Figuiére, Bourg-la-Reine; Henri Szwarc, Saint-Germain-en-Laye, all of France

[73] Assignee: ANVAR-Agence Nationale de Valorisation de la Recherche, France

[21] Appl. No.: 709,242

[22] Filed: July 27, 1976

[30] Foreign Application Priority Data

July 31, 1975 France .................................. 75.23884

[51] Int. Cl.[2] ...................... G01K 17/00; G01N 25/20
[52] U.S. Cl. ............................... 73/15 B; 73/190 R
[58] Field of Search .................. 73/15 B, 190, 191

[56] References Cited

U.S. PATENT DOCUMENTS

| | | | |
|---|---|---|---|
| 1,247,998 | 11/1917 | Parr | 73/191 |
| 3,316,750 | 5/1967 | Takeya et al. | 73/15 |
| 3,339,398 | 9/1967 | Barrall et al. | 73/15 |
| 3,593,577 | 2/1971 | Monner | 73/190 |

OTHER PUBLICATIONS

Aven, et al., "Adiabatic Specific Heat Calorimeter for the Temperange 4°–15°," Review of Sci. Inst., vol. 27, No. 8, 8/66.

*Primary Examiner*—Herbert Goldstein
*Attorney, Agent, or Firm*—Diller, Brown, Ramik & Wight

[57] ABSTRACT

A calorimeter for measuring the latent energy of a sample at a pressure of at least 1,000 bars has a test chamber enclosed in a substantially adiabatic enclosure. It has thick walls able to withstand the very high pressure, and is connected by capillary tubing to means for holding it at a set pressure. The test chamber and a reference body which is thermally equivalent to the chamber are surrounded by respective adiabatic jackets and symmetrically arranged in an isothermal enclosure which is held at a set temperature. A differential gas thermometer has bulbs in contact with the test chamber and with the reference body, and a two-input differential pressure measuring unit has each input connected by a capillary tube to one of the bulbs. The pressure measuring unit has a manometer capsule with a respective input on each side of a flexible membrane, a capacitive pickup for sensing the position of the membrane, and electronic readout means. It is enclosed in a thermally insulative case.

10 Claims, 5 Drawing Figures

CALORIMETERS FOR MAKING MEASUREMENTS AT PRESSURES ABOVE 1000 BARS

BACKGROUND OF THE INVENTION

1. Field of the Invention

The invention relates to a calorimeter suitable for measuring the latent energy of a sample at a pressure of at least 1000 bars, especially the latent heat of change of state.

2. Description of the Prior Art

Conventional calorimetric measurements at pressures close to atmospheric pressure are carried out by placing a sample in a calorimetric chamber inside an adiabatic (i.e., thermally insulated) enclosure so that there is substantially no heat exchange with the outside environment. As the heat capacity of the chamber is known, the energy changes inside it on a change of state can be measured in terms of the variation in temperature of the chamber. The sensitivity of the measurement is set by the resolution of the temperature measuring system used to detect the temperature changes, varies in inverse ratio to the heat capacity of the chamber, and is limited by heat exchanges with the outside environment. It is possible to take these heat exchanges into account, however, by plotting the temperature against time.

When the measurements must be made at high pressures, the calorimeter chamber becomes a test chamber with walls which are sufficiently thick to withstand the pressures brought into play. The heat capacity of the chamber increases with its mass. It is estimated that in order to withstand pressures as high as 1,000 to 10,000 bars the test chamber should have a mass such that the sensitivity is reduced by at least two orders of magnitude, as compared with a conventional calorimeter, except, of course, at very low temperatures close to absolute zero, where calorimetry raises very special problems. Also, measurements made by the conventional method have not gone beyond the high pressure region (i.e., pressures less than or close to 1,000 bars). Certain very special forms of apparatus have been able to go as high as 2,000 bars. Bomb calorimeters used for measuring combustion energy release very large amounts of specific energy, which does not call for high sensitivity. In the very high pressure field under consideration, it is sometimes possible to determine latent energy by indirect methods which rely on measuring parameters which have a known relationship to the internal energy of the sample.

The number of measurable parameters of a sample in a test chamber at very high pressure is very small. Thus it was considered desirable to be able to carry out calorimetric measurements on samples in very high pressure conditions so as to determine in an indirect manner physical parameters which cannot be measured directly. Among these parameters, mention may be made of the coefficient of expansion in the very high pressure field.

Studying the desirable performance of a calorimeter usable in the range of very high pressures from 1,000 to 10,000 bars for studying phenomena involving mass energy variations of the order of $10^{-2}$ joules/gm led to the realization that the means for measuring the temperature variations would have to have a resolution of at least $10^{-5}$ ° C.

SUMMARY OF THE INVENTION

One object of the invention is a calorimeter enabling change of state latent energy measurements to be made at pressures higher than 1,000 bars, and up to 10,000 bars.

Another invention is a very high pressure calorimeter with temperature measuring means having a resolution approaching $10^{-6}$ ° C.

A further object of the invention is a very high pressure calorimeter which can detect internal energy changes of the order of 0.15 joules in a working volume of about 50 cm$^3$.

With these objects in view, the invention proposes a calorimeter suitable for measuring the latent energy of a sample at a pressure of at least 1,000 bars, especially the latent energy of change of state, comprising:

a thick-walled test chamber able to withstand very high pressures, means for pressurizing said test chamber, a capillary connection between said test chamber and said pressurizing means, a reference body thermally equivalent to said test chamber, respective adiabatic jackets surrounding said test chamber and said reference body, an isothermal enclosure in which said test chamber and said reference body are symmetrically arranged, means for holding said isothermal enclosure at a set temperature, a differential gas thermometer comprising respective bulbs in thermal contact with said test chamber and said reference body, a two-input pressure measuring unit, and respective capillary connections between the inputs of said differential pressure measuring unit and said thermometer bulbs.

The test chamber may be pressurized through the capillary connection, and its thick walls are designed to withstand pressures of the order of 10,000 bars. The presence of a reference body subject to the same thermal conditions as the test chamber enables temperature differences to be measured independently of original errors in this temperature. The differential pressure measuring means may have a resolution of the order of $1.3 \times 10^{-3}$ pascal, so that with the bulbs filled with a noble gas at a pressure around atmospheric pressure a temperature measuring sensitivity of the order of $3.5 \times 10^{-6}$ ° C is achieved.

The test chamber is preferably cylindrically shaped so as to withstand very high pressures, and the reference body has the same outside shape and so the same heat capacity as the test chamber, so that their heat exchanges are equivalent. Each bulb consists of three inter-connected tubular reservoirs located in three equi-angularly spaced cylindrical bores machined longitudinally in said cylinders of the test chamber and reference body, near their periphery. Thus the temperature detected by the bulbs is the average of the temperatures of the three reservoirs. Means for providing intermittent communication between the capillary connections enables the pressures in the three bulbs to be equalized when the differential thermometer is set to zero.

The differential pressure measuring unit preferably comprises a membrane manometer with a capacitive pickup for sensing the position of the membrane and electronic means for displaying the differential pressure connected to the capacitive pickup. The membrane manometer is enclosed in a thermally insulative case which consists of nested walls which are alternately adiabatic (i.e., insulative) and diathermic (i.e., good heat conductors). The temperature of the gas on each side of the membrane is thus the same, which is an essential condition for accurate measurement of pressure.

The test chamber preferably consists of a reinforced tube with an inside diameter of substantially 16 mm, an outside diameter of substantially 150 mm, and a length of substantially 250 mm, closed at each end by a part-conical obturator held in place by a retaining block, a capillary connection to the pressurizing means running through one of the obturators. With this arrangement pressures of up to 10,000 bars can be handled in a useful volume of about 50 cm³. The test chamber and the reference body may be fitted with electrical resistances. Energy can then be injected into the test chamber or reference body from outside, to compensate for the internal energy changes of the sample.

The adiabatic jackets surrounding the test chamber and the reference body are advantageously located inside an enclosure with thermally insulative walls defining an internal space in which flows a fluid at a set temperature guided by baffles. This defines an ambient temperature for the calorimeter, and as a result reduces thermal energy losses to the outside environment, or at leat the uncontrollable losses.

The test chamber is preferably pressurized by means of a virtually incompressible liquid delivered by a pressure transformer having two aligned cylinders, one of large section and one of small section, with an intermediate stepped piston, the small section cylinder being connected to the test chamber and filled with the incompressible liquid, and the large section cylinder is supplied with hydraulic fluid by a high pressure pump.

The very high pressure is measured with the aid of a manometer consisting of a resistance measuring bridge of known type having connected into one branch a first pressure-sensitive resistance element located in the small section cylinder, and connected into a comparison branch a second resistance element similar to the first and in thermal contact with the small section cylinder. The resistance elements are, for example, spools of manganin wire.

Other objects and advantages of the invention will appear from the following description of an example of the invention, when considered in connection with the accompanying drawings.

DESCRIPTION OF THE PREFERRED EMBODIMENT

Figure 1:
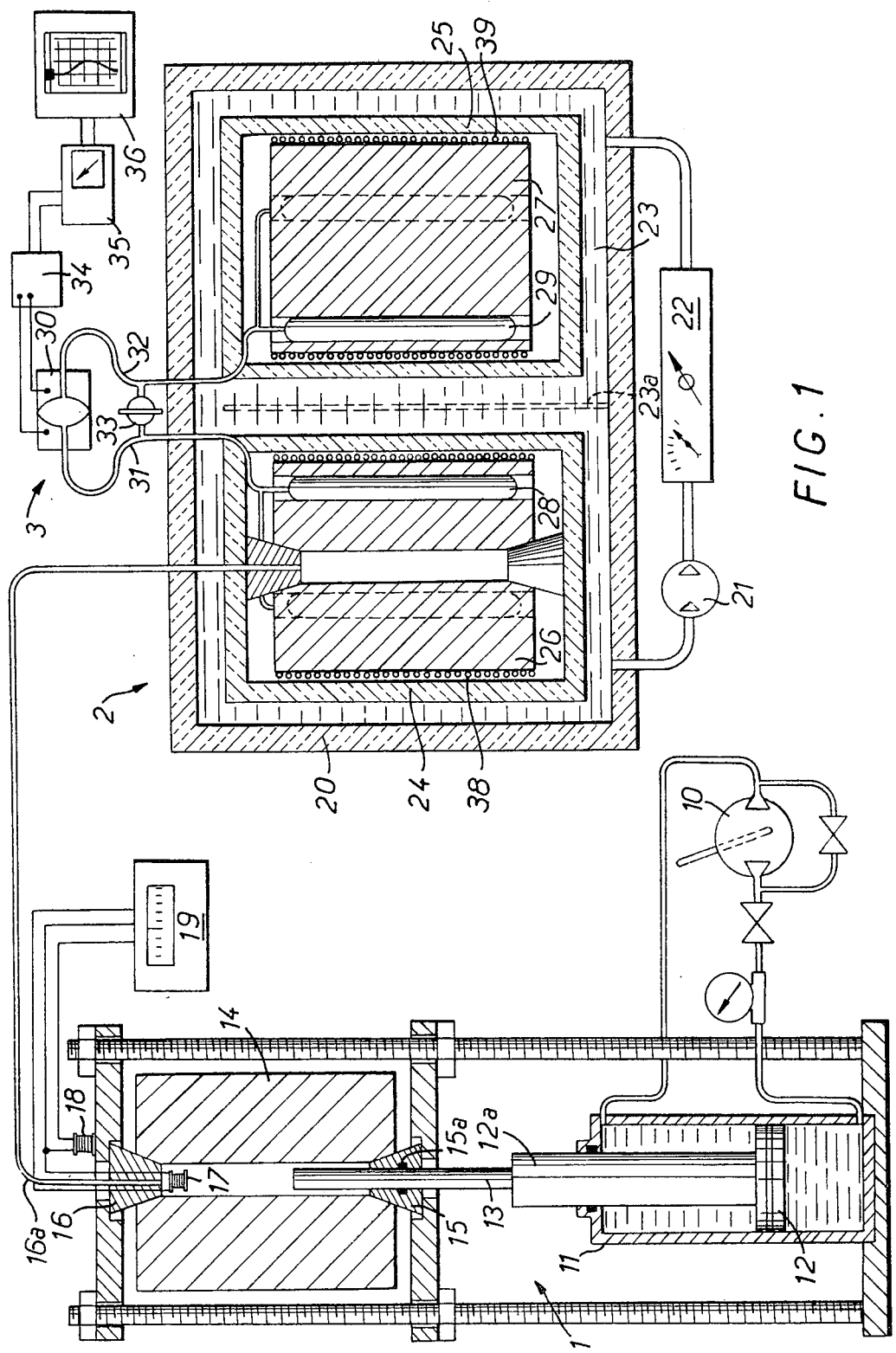
FIG. 1 is a schematic general arrangement drawing of a calorimeter in accordance with the invention.

In the selected embodiment shown in FIG. 1, the calorimeter consists of a pressurizing device generally referenced 1, a calorimetric enclosure generally referenced 2, and a temperature measuring device generally referenced 3. The pressurizing device 1 comprises a manual high-pressure pump 10 for delivering hydraulic liquid to a linear actuator comprising a cylinder 11 and a piston 12 which is extended by a piston rod 12a. The piston rod 12a is in turn extended by a plunger 13 which passes into a cylindrical very high pressure chamber 14 through a plug 15 fitted with a seal 15a. The very high pressure chamber 14 is filled with a virtually incompressible hydraulic liquid, and located in it is a spool of manganin wire 17. The spool 17, a similar spool 18 in thermal contact with the chamber 14, and a resistance bridge 19 together form a very high pressure manometer, the bridge 19 measuring the difference in resistance between the spool 17 which is subjected to the very high pressure and is connected in a first branch of the bridge 19 and the spool 18 which is at the same temperature as the spool 17 and is connected in a comparison branch of the bridge 19.

The calorimetric enclosure 2 comprises an outer heat insulative envelope 20 which defines an internal space 23 in which a thermostatic liquid flows under the influence of a pump 21, the temperature of the liquid being controlled to ± 0.05° C and set to a value between −30° C and +150° C by a conventional thermostat 22. In the internal space 23 are arranged a test chamber 26 and a reference body 27 which have substantially the same mass and outside geometrical configuration, and which are enclosed in respective heat insulative jackets 24 and 25. These thermally insulative jackets 24 and 25 and the thermally insulative envelope 20 are made from expanded cork with a thin metal sealing skin. The jackets 24 and 25 are symmetrically arranged in the space 23 so that the heat losses from the test chamber 26 and the reference body 27 are as nearly equal as possible. A baffle system shown symbolically at 23a ensures that the thermostatic liquid flows all over the surfaces of the jackets 24 and 25. The test chamber 26, which will be described in more detail later, and the reference body 27 comprise housings for respective thermometer bulbs 28 and 29. The bulbs 28 and 29 enclose dry nitrogen at substantially atmospheric pressure and are connected by means of respective capillary connections 31 and 32 to the two inputs of a differential temperature measuring device 3 which will be described in more detail later.

Figure 2:
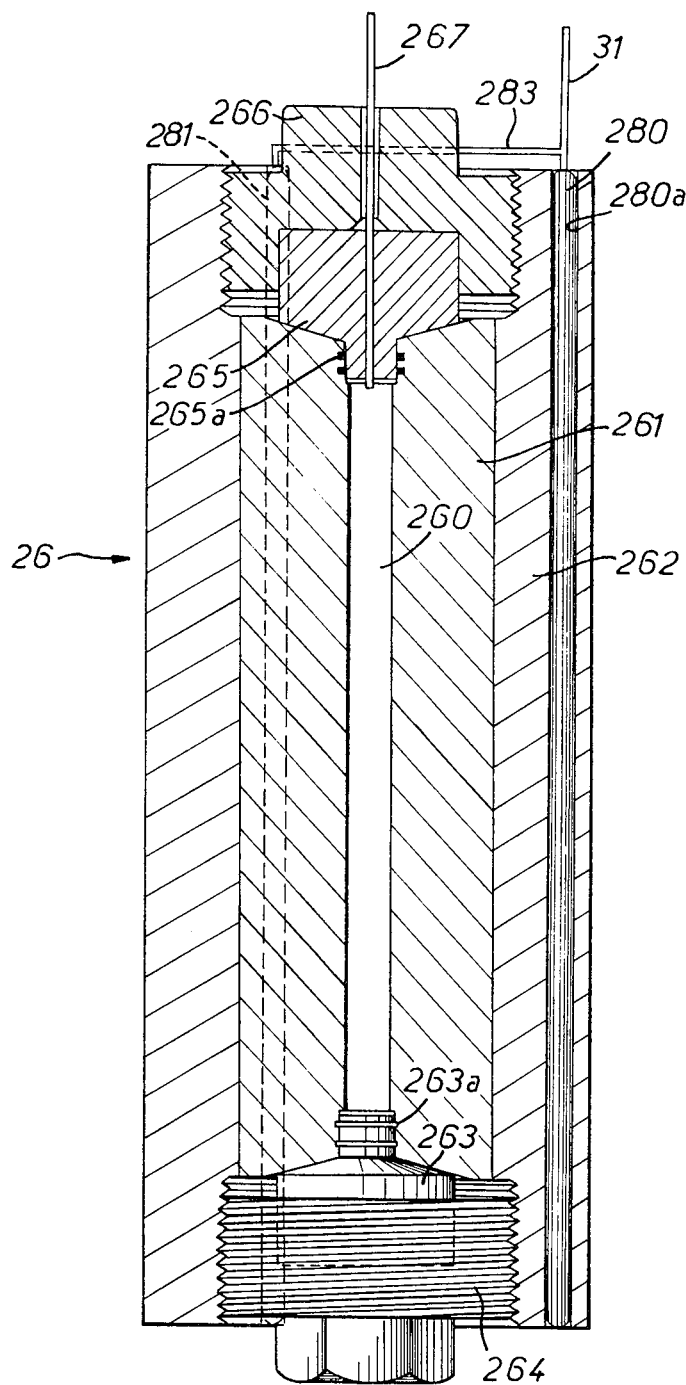
FIG. 2 is a longitudinal cross-section through a test chamber.
Figure 3:
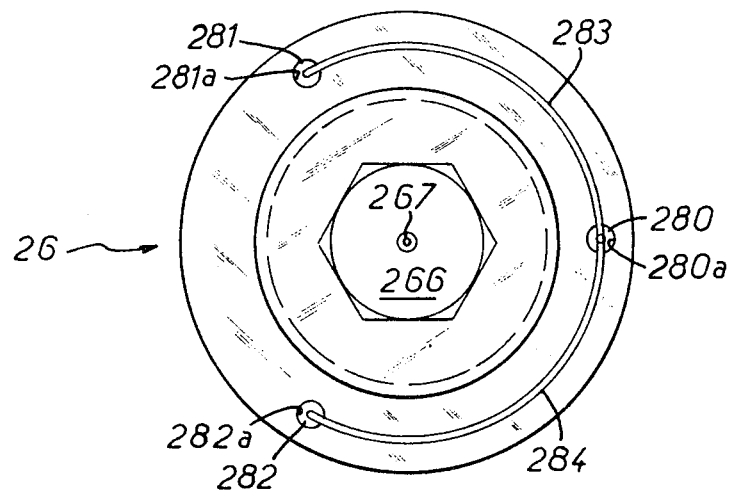
FIG. 3 is a plan view of the chamber shown in FIG. 2.

Referring to FIGS. 2 and 3, the test chamber 26 has a cylindrical channel 260 bored out of a thick steel cylinder 261, which is fitted with a tubular reinforcing member 262. The channel 260 is closed at both ends by part-conical obturators 263 and 265 fitted with respective seals 253a and 265a. These obturators are held in place by respective retaining blocks 264 and 266 which screw into the reinforcing member 262. A capillary tube 267 passes through the upper obturator 265, being the end of the capillary connection 16a of FIG. 1. Near the periphery of the reinforcing tube 262 there are machined three cylindrical bores 280a, 281a and 282a parallel to the axis of the channel 260 and extending along the three edges of an equilateral triangular prism. In these bores are inserted cylindrical reservoirs 280, 281 and 282 which are inter-connected by means of capillary tubes 283 and 284 in the shape of circular arcs, the three reservoirs together making up the bulb 28 of FIG. 1. The reference body 27 is of the same shape as the test chamber 26 and is provided in just the same way with three reservoirs which form the bulb 29. It should be noted that the very high pressure chamber 14. (FIG. 1) is of the same size as the chamber 26 and reinforced in the same way, but does not have any bores for thermometer bulbs.

To enable measurements to be made at up to 10,000 bars, the diameter of the channel 260 is about 16 mm and its length between the obturators 263 and 265 is about 230 mm, while the outside diameter of the reinforcing tube 262 is about 150 mm and its length about 400 mm. The useful volume of the channel 260 of the test chamber 26 is about 50 cm³, while the mass of the test chamber exceeds 50 kg.

Figure 4:
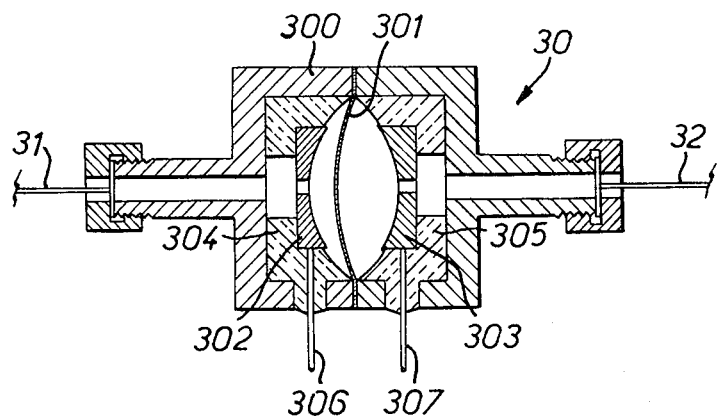
FIG. 4 is a schematic cross-section through a differential pressure measuring unit provided with a capacitive pickup.

The capillary connections 31 and 32 (FIG. 1) which lead to the temperature measuring device 3 can be put in communication with each other by means of a tap 33 of the type used in chromatography, and lead to a differential pressure pickup 30 which is shown schematically in FIG. 4. The capillary connections 31 and 32 open into a metal capsule 300, one on each side of a very thin and flexible metal wall 301. Symmetrical electrodes 302 and 303 are also placed one on each side of the flexible metal wall 301, and are held in place in the capsule 300 by respective blocks 304 and 305 of electrically insulative material. Leads 306 and 307 enable them to be connected to electronic means for displaying the differential pressure, comprising a capacitance bridge 34 (FIG. 1), deviation measuring apparatus 35, and a chart recorder 36. The pickup 30, capacitance bridge 34, measuring apparatus 35 and recorder 36 make up a known type of differential pressure measuring unit which can measure pressure differences with a resolution of the order of $10^{-5}$ Torr, i.e., $1.23 \times 10^{-3}$ pascals.

Figure 5:
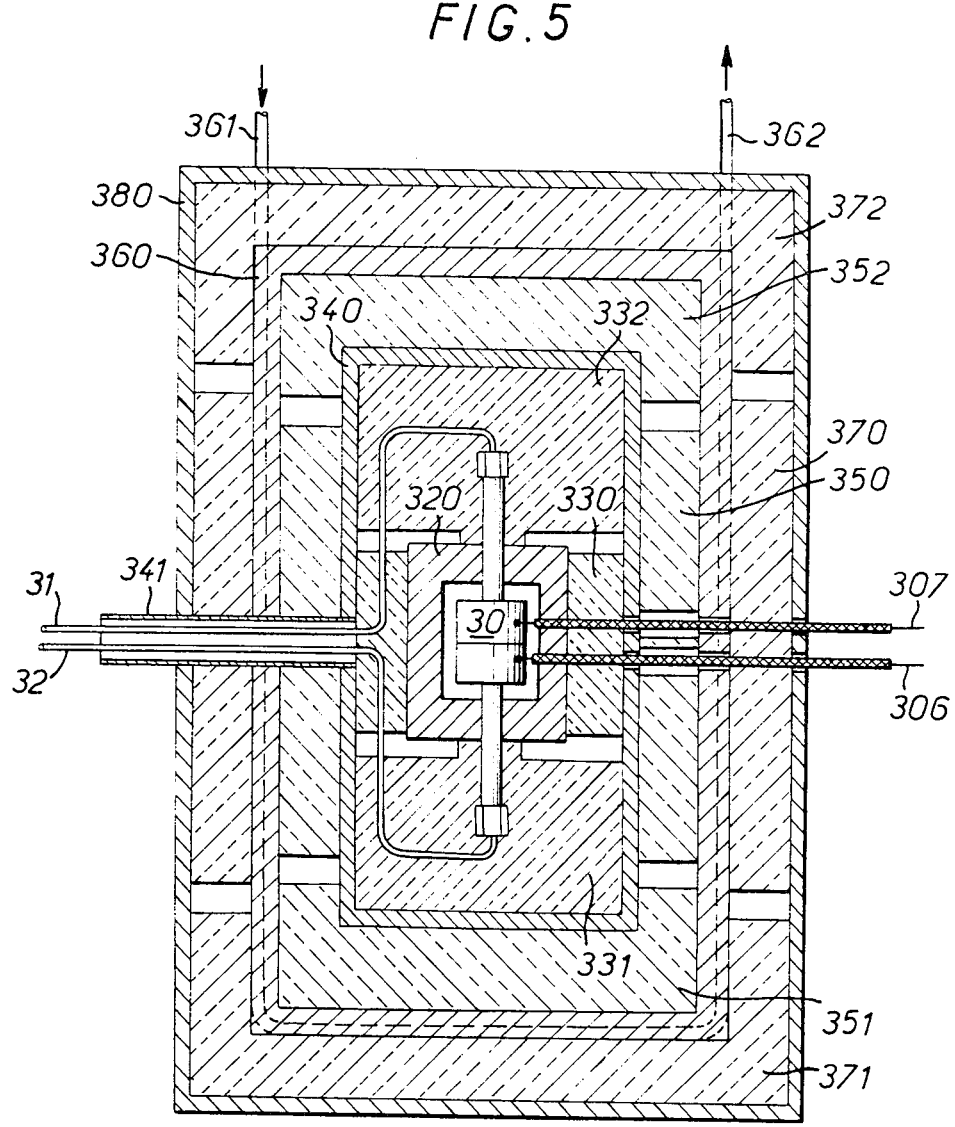
FIG. 5 shows the arrangement of the capacitive pickup of FIG. 4 in the thermally insulative case.

The pickup 30 is situated in a thermally insulative case shown in FIG. 5 and which is composed of nested walls which are alternately of insulative plastics foam (adiabatic) and copper or aluminum (diathermic). Starting from the pickup 30, one finds a cylindrical copper wall 320 in which the central part of the pickup 30 rests; the armored conductors 306 and 307 connecting it to the capacitance bridge pass through this wall 320, and the outside layer of these conductors is embedded in the wall. The next adiabatic wall consists of a sleeve 330 and two end plugs 331 and 332 containing the start of the capillary connections 31 and 32. Around this adiabatic wall is a diathermic wall 340 which supports a flue 341 for the capillary connections 31 and 32 to pass out through. Around this wall 340 is an adiabatic wall consisting of a sleeve 350 and two plugs 351 and 352. Around this adiabatic wall is a duralumin wall 360 fitted with tubing in which a thermostatic fluid flows from an inlet 361 to an outlet 362. This thermostatic fluid sets the temperature of this diathermic wall 360 and therefore the general temperature of the case 3. Around the wall 360 is an adiabatic wall comprising a sleeve 370 and two plugs 371 and 372, and finally an outer duralumin wall 380.

To bring the calorimeter in accordance with the invention into use, the test chamber 26 (FIG. 1) is pressurized by pumping in incompressible liquid from the very high pressure chamber 14 through the capillary connection 16a. Because of the stepped arrangement of the large section piston 12 and the small section plunger 13, the pressure which is established in the chamber 14 is a multiple of the pressure on the lower face of the piston 12, the multiplication ratio being substantially equal to the ratio of the area of the large section of piston 12 to the small section of plunger 13. The small section is of the order of 2 cm² and the large section of the order of 28 cm², so that if the pump 10 delivers hydraulic liquid at a pressure of around 700 bars a pressure of 10,000 bars is obtained in the chamber 14 and in the test chamber 26.

Under this pressure the spool 17 is slightly and elastically compressed, the effect of the resulting dimensional deformation being to vary the resistance of the spool, which has a nominal resistance of 120 ohms. The spool 17 is connected into a first branch of the resistance bridge 19, while the spool 18 which is similar to the spool 17 and at substantially the same temperature is connected into a comparator branch. The bridge 19 detects the variation in the resistance of the spool 17, and responds by displaying a deviation which is representative of the pressure in the chamber 14 and test chamber 26, with a resolution of the order of 2 bars and an accuracy of the order of 1%.

In the calorimeter enclosure 2 the general temperature is set by the temperature of the thermostatic fluid in the internal space 23, this temperature being set by the thermostat 22 which is appropriately adjusted and which is stable to within 0.05° C. Because the masses of the test chamber 26 and the reference body 27 are both in the region of 50 kg, and because of the thermal conductivity of the adiabatic jackets 24 and 25, the thermal time constant is such that the thermostatic enclosure reaches a state of equilibrium in about 30 hours.

The volume of each of the three cylindrical reservoirs which make up the bulbs 28 and 29 is about 20 cm³, so that in each bulb 28 and 29 there is a volume of dried nitrogen of about 60 cm³. When thermal equilibrium is established in the calorimeter enclosure 2 the tap 33 is opened, so that there is a pressure equilibrium in the capsule 30 which corresponds to the thermal equilibrium in the calorimeter enclosure 2. As the internal volume of the capsule 30 is about 3 cm³, the temperature inside the capsule must be uniform to within better than $4 \times 10^{-5°}$ C if the sensitivity of $3.5 \times 10^{-6°}$ C for the measurement of the temperature difference between the test chamber 26 and the reference body 27 is to remain meaningful. This uniformity of the temperature within the capsule 30 is achieved by means of the arrangement shown in FIG. 5, in which the diathermic walls 360, 340 and 320 are each at a virtually uniform temperature because of their high thermal conductivity and because the adiabatic baffles limit transfer of thermal energy outside the diathermic walls to very low values, so limiting the energy flux within the diathermic walls to similarly low values. The uniformity of temperature increases from wall 360 to wall 320.

The differential temperature measurement sensitivity of $3.5 \times 10^{-6°}$ C is achieved by using a differential pressure pickup with a sensitivity of $1.3 \times 10^{-3}$ pascals operating at an absolute pressure of about $10^5$ pascals (about 1 atmosphere) with a perfect gas (dried nitrogen) which has a coefficient of expansion of $1/273 = 3.66 \times 10^{-3}$ per centigrade degree.

To make use of the calorimeter in accordance with the invention, the sample is placed in the test chamber 26, bare if there is no risk of it reacting with the virtually incompressible hydraulic liquid used for the pressurizing, or enclosed in a thin sachet of metal or Teflon if there is a risk of reaction. The test chamber is filled with the pressurizing liquid and then closed by fitting the obturator 263 and screwing down the retaining block 264 (FIG. 2). The chamber 26 must be filled with the pressurizing liquid without introducing any air, as changes of state of the latter on pressurizing the chamber could falsify the results. The test chamber is in its jacket 24 and the latter is the calorimetric enclosure 2.

Then, with the tap 33 open, the calorimetric enclosure 2 is set to the required temperature by circulating the thermostatic liquid through the internal space 23 with the pump 21, the temperature being determined by the setting of the thermostat 22. The chamber 26 is then raised to the maximum pressure foreseen for the study of the sample, using the pump 10, and the pressure is measured with the bridge 19. The measurements are almost always carried out in order of decreasing pressure to avoid liquid from the very high pressure chamber 14 reaching the test chamber during the measurement, through the capillary connection 16a, because of the non-zero compressibility of the liquid and the elasticity of the walls of the chamber 26, any such liquid naturally being at a different temperature to the calorimeter enclosure. There is then a pulse for the temperature in the enclosure to reach equilibrium, which registers, after the tap 33 is closed, as a linear variation of temperature with time which is recorded on the chart recorder 36. The straight line obtained, called the zero line, is slightly inclined to the time axis and represents residual losses from the calorimeter enclosure. Varying the pressure in the test chamber 26 by varying the pressure in the linear actuator 11 produces a discontinuity in the curve on the recorder 36, resulting from variations in the temperature in the test chamber consequent upon changes of state produced in the chamber. These changes of state are the sum of the individual changes of state of the sample, the pressurizing liquid (compression or expansion), and the walls of the chamber (elastic stresses). After about 20 minutes the recorder 36 shows another straight line which is parallel to the first, the distance between the two lines representing the latent energy of change of state.

The coefficient of proportionality between the temperature shifts read on the measuring apparatus 35 and recorded on the chart recorder 36 and the internal energy variations in the chamber 26 can be determined by calibration of the apparatus prior to the measurements, as can the corrections to be made to take into account the compressibility of the pressurizing liquid and the elasticity of the walls of the chamber 26. Calibration of the internal energy variations canbe effected by causing an isothermal change in the pressure of a perfect gas in the test chamber, for example dry nitrogen at a pressure of a few tens of bars. The corrections for the compressibility of the pressurizing liquid and the elasticity of the walls of the chamber 26 are determined by taking measurements without a sample. It will be evident that if the sample is a liquid the test chamber 26 and the very high pressure chamber 14 will be filled with this liquid, so that the liquid sample will act as the pressurizing liquid, and there will be no need to correct for the compressibility of the liquid, since it is the variation of latent energy of the liquid under pressure which is just what one is looking for.

An interesting improvement can be made to the calorimeter by winding electrical resistances 38 and 39 on the test chamber 26 and the reference body 27, respectively, and connecting these resistances to an external source of electrical energy. With these resistances known amounts of energy can be injected into the test chamber 26 or the reference body 27. The slope of the zero lines can thus be reduced and the calorimeter calibrated, and it may be possible to shorten and time taken to reach thermal equilibrium. With resistances of 50 ohms and a supply voltage of one volt the power injected is 20 milliwatts, i.e., energy is injected at a rate of 20 millijoules per second.

One calorimeter made in accordance with the invention had the following characteristics:

| | |
|---|---|
| test chamber volume | 50 cm$^3$ |
| test chamber mass | 50 kg (approx) |
| test chamber heat capacity | 2.15 kJ/° C |
| differential thermometer sensitivity | 4 × 10$^{-6}$° C |
| maximum working pressure | 10 000 bars |
| resolution of working pressure measurement | 2 bars |
| accuracy of working temperature measurement | 0.05° C |
| energy resolution | 10$^{-2}$ joules |

With this calorimeter it is possible to determine the coefficient of expansion of liquids such as benzene under very high pressures, the latent energy of crystallization of solutions and liquids, and the latent energy of transformation of the crystalline phase of solids. Because of its high sensitivity and its universal application, it can be used to carry out a wide range of calorimetric measurements under very high pressures.

It will be understood that various changes in the details, materials and arrangement of parts which have been described herein for the purpose of explaining the nature of the invention may be made by those skilled in the art without departing from the scope of the invention as expressed in the following claims.

We claim:
1. A calorimeter suitable for measuring the latent energy of a sample at a pressure of at least 1,000 bars, especially the latent energy of change of state, comprising:
   a thick walled test chamber able to withstand very high pressure,
   means for changing the state of a sample in said test chamber essentially comprising means for pressurizing said test chamber including pressure measuring means,
   a connecting means having a small flow section disposed between said test chamber and said pressurizing means,
   a reference body thermally equivalent to said test chamber,
   respective thermally insulating jackets surrounding said test chamber and said pressurizing means,
   an isothermal enclosure in which said test chamber and said reference body are symetrically arranged,
   means for holding said isothermal enclosure at a set temperature,
   a differential gas thermometer comprising respective bulbs in thermal contact with said reference body and thick walls of said chamber externally to this latter, and
   a two inputs differential pressure measuring unit, each input respectively connected to said thermometer bulbs by capillary connections, where the sensitivity of said differential pressure unit is such that temperature differences lesser than 10$^{-5}$° C, may be detected within the range − 30° to + 150° C.

2. A calorimeter as set forth in claim 1, wherein said test chamber and said reference body are of generally cylindrical shape, three equi-angularly spaced cylindrical bores are provided longitudinally in each of said cylinders, near the periphery thereof, and each of said bulbs consists of three inter-connected tubular reservoirs located in said bores.

3. A calorimeter as set forth in claim 1, comprising means for providing intermittent communication between the capillary connections of said bulbs to said differential pressure measuring unit.

4. A calorimeter as set forth in claim 1, wherein said differential pressure measuring unit comprises a flexible membrane, a manometer capsule with a respective inut on each side of said membrane, a capacitive pickup for sensing the position of said membrane, and electronic means connected to said capacitive pickup for displaying the differential pressure, said capsule being enclosed in a thermally insulative case consisting of nested walls which are alternately adiabatic and diathermic.

5. A calorimeter as set forth in claim 1, wherein said test chamber comprises a reinforced tube having an inside diameter of substantially 16 mm, an outside diameter of substantially 150 mm, and a length of substantially 250 mm, said tube being closed at each end by a frusto conical obturator which is held in place by a retaining block, a connecting means having a small flow section connection to said pressurizing means passing through one of said obturators.

6. A calorimeter as set forth in claim 1, comprising respective similar electrical resistances wound round said test chamber and said reference body, and electrical connections extending therefrom to the outside of said calorimeter.

7. A calorimeter as set forth in claim 1, comprising an enclosure with thermally insulative walls which define an internal space in which are disposed said thermally insulating jackets enclosing said test chamber and said reference body, means for causing a fluid at a set temperature to flow through said internal space, and baffles for guiding said fluid as it flows through said internal space.

8. A calorimeter as set forth in claim 1, in which said pressurizing means compris a hydraulic pump and a pressure transformer having two aligned cylinders, of small and large cross-section, respectively, with an intermediate stepped piston, said large section cylinder being supplied with hydraulic fluid bu said pump and said small section cylinder being connected to said test chamber by capillary means, said small section cylinder and said test chamber both being filled with a liquid which is practically incompressible.

9. A calorimeter as set forth in claim 8, comprising pressure measuring means connecting of a resistance measuring bridge, a first pressure-sensitive resistance element located in said small section cylinder and connected into a first branch of said bridge, and a second resistance element similar to said first resistance element, in thermal contact with said small section cylinder and connected into a comparison branch of said bridge.

10. A calorimeter as set forth in claim 9, wherein said first and second reistance elements are coils of manganin wire.

* * * * *